US008473041B2

(12) United States Patent
Bartnik et al.

(10) Patent No.: US 8,473,041 B2
(45) Date of Patent: Jun. 25, 2013

(54) CARDIOGRAPHY SYSTEM AND METHOD USING AUTOMATED RECOGNITION OF HEMODYNAMIC PARAMETERS AND WAVEFORM ATTRIBUTES

(75) Inventors: Daniel Bartnik, Eden Prairie, MN (US); Paulita LaPlante, Inver Grove Heights, MN (US); Richard L. Summers, Madison, MS (US); Victor E. Kimball, St. Louis Park, MN (US)

(73) Assignee: Vasamed, Inc., Eden Prairie, MN (US)

( * ) Notice: Subject to any disclaimer, the term of this patent is extended or adjusted under 35 U.S.C. 154(b) by 40 days.

(21) Appl. No.: 13/019,378

(22) Filed: Feb. 2, 2011

(65) Prior Publication Data

US 2011/0152638 A1    Jun. 23, 2011

Related U.S. Application Data

(63) Continuation of application No. 12/282,468, filed as application No. PCT/US2007/006253 on Mar. 12, 2007, now abandoned.

(60) Provisional application No. 60/781,135, filed on Mar. 10, 2006.

(51) Int. Cl.
*A61B 5/04* (2006.01)

(52) U.S. Cl.
USPC .......................................................... 600/513

(58) Field of Classification Search
USPC .................................................. 600/509, 513
See application file for complete search history.

(56) References Cited

U.S. PATENT DOCUMENTS

| 6,520,917 B1 | 2/2003 | Kunig et al. |
| 6,767,329 B2 | 7/2004 | Amano et al. |
| 7,225,013 B2 | 5/2007 | Geva et al. |
| 7,616,991 B2 | 11/2009 | Mann et al. |
| 2005/0131308 A1 | 6/2005 | Chio et al. |

*Primary Examiner* — Brian T Gedeon
(74) *Attorney, Agent, or Firm* — Barbara A. Wrigley; Oppenheimer Wolff & Donnelly, LLP

(57) ABSTRACT

A cardiography system and method using automated recognition of hemodynamic parameters and waveform attributes is provided. The cardiography system and method includes at least one sensor, a knowledge base and a processing device. The at least one sensor provides a waveform signal and a hemodynamic parameter input. The knowledge base includes data corresponding to various disease states. The processing device receives the waveform signal and hemodynamic parameter input from the sensor, identifies waveform attributes on the waveform signal, measures the waveform attributes, accesses the knowledge base, cross-references the waveform attributes and the hemodynamic parameters with data in the knowledge base, and outputs a suggested likelihood of a particular disease state. The knowledge base optionally includes goal-directed therapies associated with particular disease states for providing suggested goal-directed therapies based on the cross-referencing of the waveform attributes and the hemodynamic parameters with the knowledge base.

32 Claims, 11 Drawing Sheets

CARDIOGRAPHY SYSTEM AND METHOD USING AUTOMATED RECOGNITION OF HEMODYNAMIC PARAMETERS AND WAVEFORM ATTRIBUTES

The present invention is a continuation of U.S. patent application Ser. No. 12/282,468, filed Sep. 10, 2008, which is a U.S. national stage application of PCT/US07/06253, filed Mar. 12, 2007, which is a non-provisional application of U.S. Provisional Patent Application 60/781,135, filed Mar. 10, 2006.

BACKGROUND OF THE INVENTION

1. Field of the Invention

The present invention relates to a method and system for measuring and reporting time based parameters associated with heart activity. More particularly, the present invention relates to a cardiography system and method using automated recognition of hemodynamic parameters and waveform attributes for monitoring and recording signals derived from heart valve activity and guiding goal-directed therapy by correlating cardiovasculograms (CVG) with waveform and hemodynamic data stored in local memory.

2. Discussion of the Related Art

Cardiac output and circulatory flow are a balance of the pumping ability of the heart. Congestive heart failure (CHF) is a condition in which the cardiac output is unable to meet the metabolic demands of the body. This condition can vary in severity from a simple elevation in cardiac filling pressures, known as compensated failure, to severe hypoxia and edema, known as decompensated failure.

CHF is thought to result from a failure in the contractile elements of the heart during the systolic phase of the cardiac cycle, which is known as systolic congestive heart failure. Systolic CHF is characterized clinically by an ejection fraction of less than 30%. Systolic CHF can be a result of a myriad of possible pathologies affecting the contractile ability of the heart muscle including myocardial infarction, cardiomyopathies, and metabolic disorders. Management of this disorder has evolved over recent years and is highly dependent upon the severity of the condition. Most treatment regimens involve attempting to increase systolic contractility or focusing on hemodynamic manipulations that allow the heart to take a passive role in circulatory control.

More recently it has been recognized that limitations in cardiac filling and venous return during diastole can also result in an abnormal circulatory flow, which is known as diastolic congestive heart failure. Diastolic CHF is defined as the condition in which there is evidence of the clinical signs of CHF in the presence of normal systolic functioning. This condition occurs in as many as 30% of patients presenting with heart failure. Some of this dysfunction may be due to a stiff myocardium limiting the passive phase of diastolic filling. However, the majority of dysfunction is caused by lengthening of isovolumic myocardial relaxation or isovolumic relaxation times (IVRT). Myocardial relaxation is an energy-dependent, active process that is mainly unconstrained by preload and afterload considerations. Ventricular hypertrophy is often the end result of long-standing hypertension and is commonly responsible for delays in IVRT due to abnormalities in calcium kinetics. Researchers have shown that an IVRT greater than 0.125 sec is indicative of diastolic dysfunction. Patients presenting with CHF due to diastolic dysfunction may not respond to traditional therapies. These traditional therapies can even be detrimental to patients presenting with CHF due to diastolic dysfunction. Patients with evidence of acute decompensation secondary to a diastolic mechanism may have worsening of symptoms, hypotensive response, and reduced cardiac output with the typical off-loading treatments of diuretics or preload reducing medication. As a result, it is important to identify accurately which type of CHF a patient is presenting, in order to identify appropriate goal directed therapies.

The analysis of waveforms obtained from physiologic monitoring is a common practice in medicine. Clinicians have used waveform patterns obtained from electrocardiography, capnography, cardiotocography, and spirometry to assist in the diagnostic assessment of patient pathology. The unassisted, human interpretation of CVG pattern recognition and differentiation of these waveforms is a clinical art form that requires experience and skilled expertise. However, automated computerized interpretations of waveforms based upon specific segmental waveform criteria have been widely used in medicine to assist clinicians in the diagnostic process. In the field of electrocardiography, the interpretative waveform criteria have been developed based upon evidence from clinical correlations and standardized for specific diagnoses. Proprietary computerized algorithms use these criteria for their electrocardiographic interpretation.

Clinical evidence supports the use of waveform analysis and diagnostic interpretation in the field of impedance cardiography (ICG). ICG is a technique used to provide non-invasive monitoring and analysis of a patient's cardiac performance. ICG systems measure and report several time-based parameters related to cardiac performance, including the pre-ejection period (PEP) and the left ventricular ejection time (LVET). ICG systems produce ICG signals from monitoring movement and volume of blood as a result of the heart contracting. Exemplary ICG systems are shown and described in Ackmann et al., U.S. Pat. No. 5,178,154; and Reining, U.S. Pat. No. 5,505,209 both incorporated by reference herein in their entireties. The '154 and '209 patents disclose the use of electrode bands placed on a patient with high frequency, low magnitude electrical current applied to the electrode bands. Voltage changes across the bands are read, filtered and converted into thoracic impedance. The ICG system displays the thoracic impedance signal versus time to create a visual display of the ICG signal. The '154 patent further discloses that ICG systems can receive conventional electrocardiograph signals, signals from blood pressure monitors, signals from piezoelectric microphones attached to the chest of the patient and the like. These signals, in addition to thoracic impedance, can be stored and averaged via a memory storage device connected to the ICG system.

A CVG is a waveform produced by the processing of impedance cardiography (ICG) signals and which may also be supported by processing other signal inputs such as electrocardiography (ECG) signals, phonocardiography (PCG) signals and other hemodynamic signals. The CVG waveform in combination with the accompanying electrocardiograph, describe the electromechanical events of the cardiac cycle. The CVG is a signature waveform and can be interpreted by physicians in much the same way as electrocardiograms are interpreted. Despite improvements in ICG systems and/or signal processing, there have been no advances in the methodology of automated waveform analysis for ICG systems. Specifically, there exists a need for using CVG waveforms in an automated system to differentiate decompensated heart failure from other common clinical conditions and to further distinguish between diastolic and systolic forms of heart failure.

Phonocardiography (PCG) is a non-invasive technique used by healthcare professionals to monitor cardiac performance. PCG systems generate PCG signals by monitoring the opening and closing of valves within a patient's heart. PCG systems use a microphone that records sounds of heart valve activity, similar to electronic stethoscopes known in the art, in order to provide indications of aortic heart valve opening (shown as S1 on FIG. 1) and aortic heart valve closure (shown as S2 on FIG. 1).

Another non-invasive system used to monitor heart activity is an electrocardiogram (ECG) system. ECG signals are electrical signals that are generated from the depolarization and repolarization of myocardial cells in a patient's heart. ECG systems are known to include a first external electrode attached to a patient's skin, a second external electrode attached to a patient's skin and optionally a third external electrode attached to a patient's skin. An amplifier is used to monitor electrical heart activity signals at the first and second electrodes and generate an ECG signal based on the difference between these activity signals. The optional third electrode can be used to reduce or offset noise in the ECG signal.

Still another non-invasive system used by healthcare professionals to monitor cardiac performance is a blood pressure system. A patient's blood pressure is monitored according to known techniques and converted into a blood pressure signal. The blood pressure signal is then displayed on a blood pressure waveform. Blood pressure waveforms, similar to PCG waveforms, can be used by healthcare professionals to identify heart valve closure because the dicrotic notch in blood pressure waveforms reflects closure of the aortic heart valve. Other exemplary systems using signals that have pulsatile characteristics resulting from the contraction of the heart are shown and described in Kimball et al., U.S. Pat. No. 6,763,256, herein incorporated by reference in its entirety.

The PEP is defined as the period of isovolumic ventricular contraction when the patient's heart is pumping against the closed aortic valve. In ICG systems, the PEP is measured starting with the initiation of the QRS complex (the "Q" point on FIG. 1) of the ECG signal and ending with the start of the mechanical systole as marked by the initial deflection of the systolic waveform (the "B" point on FIG. 1) of the ICG signal coincident with the opening of the aortic valve or the onset of left ventricular ejection into the aorta. The LVET begins at the end of the PEP and ends at the closure of the aortic valve (the "X" Point on FIG. 1) when ejections ends.

It is important that ICG systems provide accurate results for the PEP and the LVET because healthcare professionals utilize the results of these parameters when making decisions about patient diagnosis and care. Additionally, accurate determination of the PEP and the LVET time intervals is also required for accurate and reliable determination of subsequent and dependent parameters. For example, results from determination of the PEP and the LVET are used to calculate the systolic time ratio (STR), where STR=PEP/LVET. While many ICG systems use proprietary equations for determination of stroke volume (SV), it is commonly known that SV equations frequently incorporate LVET as an input parameter. Accordingly, accurate determination of time intervals between the PEP and the LVET is also necessary for accurate determination of SV, and subsequently for cardiac output (CO) based on SV and heart rate (HR), where CO=SV*HR.

Many CVG waveforms, particularly for healthy individuals, provide sufficient detail so that ICG systems can identify the location of the aortic valve opening and closing, or the LVET, with a high degree of confidence. For example, in the CVG waveform depicted in FIG. 1, opening, B point, of the aortic valve and closing, X point, of the aortic valve are easily identifiable. When comparing the CVG waveform with the phonocardiograph (PCG) waveform (both shown in FIG. 1), marking of the B point in the CVG waveform is confirmed by the time-associated presence of the S1 component in the PCG waveform. Similarly, marking of the X point in the CVG waveform is confirmed by the time associated presence of the S2 component in the PCG waveform.

A number of parameters, including but not limited to cardiac output, thoracic fluid content, Heather Index, and the like, have been derived from impedance signals to assist in the diagnosis of decompensated heart failure. Traditionally, however, ICG systems only analyze attributes of the impedance signal when determining the location of heart valve activity. Some ICG systems may record and display PCG signals, blood pressure signals, and/or other signals having pulsatile characteristics resulting from contraction of the heart, but these ICG systems do not integrate these signals into the automatic location of heart valve activity. ICG systems alone often lack sufficient information to accurately and reliably determine the PEP and the LVET because of confounding information related to opening and closing of the patient's aortic valve. For example, in the CVG waveform depicted in FIG. 2, closure, X point, of the aortic valve could be any of several depressions following the peak blood flow, C. The known algorithm selected the deepest depression in the CVG waveform because the aortic valve closure is often thought to produce the strongest negative signal. However, when the CVG waveform depicted in FIG. 2 is compared with the PCG waveform depicted in FIG. 2, the aortic valve closure, X point, should have been one of the later depressions in the CVG waveform in order to correlate with the time associated presence of the S2 component in the PCG waveform. Accordingly, there is a need for an impedance cardiography method and system for automated correlation of impedance signals from ICG systems with other signals derived from heart valve activity in order to provide more accurate identification of heart valve activity.

Many of the specific segmental criteria used in this comprehensive pattern recognition are based upon well-established characterizations of changes in systolic and diastolic function as determined from elements of the impedance cardiogram.

It is known that experienced healthcare professionals can recognize, or diagnose, certain disease states by analyzing hemodynamic parameters in combination with visual displays of ICG signals provided by some ICG systems. Experienced healthcare professionals can easily recognize the systolic and diastolic segments of these visual displays in addition to other attributes such as amplitude, shape, tone, slope and timing, in combination with hemodynamic parameters. Analysis of these attributes allows experienced healthcare professionals to ascertain an underlying disease state. However, variations in ICG signal attributes makes non-automated diagnosis difficult.

It is also known that some ICG systems provide minimal waveform information. When using these types of systems, healthcare professionals must rely largely on numeric parameters to make a diagnosis because these systems do not provide other information. With ICG systems that do not display waveforms, even experienced healthcare professionals may be unable to make a diagnosis. Based on the foregoing, there exists a need for an automated cardiography method and system for measuring cardiovasculograms that provides suggested underlying conditions based on correlating the recognized waveform attributes and hemodynamic parameters with waveform attributes and hemodynamic parameters associated with particular underlying conditions.

SUMMARY OF THE INVENTION

The present invention provides a cardiography method and system for measuring cardiovasculograms including signals derived from heart valve activity that are time coordinated with ICG signals, such that the signals derived from heart valve activity are used as confirmation that the cardiography system is accurately positioning heart valve activity. The present invention also provides improved accuracy in reported values such as PEP, LVET, STR, SV and CO. The present invention also provides improved accuracy of graphic presentation of heart activity when the graphic presentation includes identifying heart valve activity. The present invention categorizes and saves waveform attributes and hemodynamic parameters correlated with various patient disease states such that measured waveform attributes and hemodynamic parameters can be matched with the categorized and saved data in order to provide automated diagnoses. The present invention provides physicians with assistance in achieving goal directed therapy.

The present invention includes a cardiography system for automated recognition of hemodynamic parameters and waveform attributes including one or more sensors for providing one or more waveform signals and a hemodynamic parameter input; a knowledge base for providing data corresponding to various disease states; a processing device connected to the sensor(s) and the knowledge base, where the processing device receives the waveform signal(s) and the hemodynamic parameter input, identifies waveform attributes on the waveform signal, measures the waveform attributes, measures the hemodynamic parameter input, cross-references the waveform attributes and the hemodynamic parameter input with the knowledge base, and outputs a suggested likelihood of a particular disease state based on the cross-referencing. The system in accordance with the present invention optionally includes a display device for displaying the output. The knowledge base of the present invention can also include goal-directed therapies associated with particular disease states for providing suggested goal-directed therapies based on the cross-referencing of the waveform attributes and the hemodynamic parameters with the knowledge base.

The present invention also includes a method for automated recognition of hemodynamic parameters and waveform attributes to assess disease states including the steps of providing one or more sensor for generating one or more waveform signal and a hemodynamic parameter input; providing a knowledge base having data corresponding to various disease states; providing a processing device in communication with the sensor(s) and the knowledge base, where the processing device is used for receiving the waveform signal(s) and the hemodynamic parameter input, identifying waveform attributes on the waveform signal, measuring the waveform attributes, measuring the hemodynamic parameter input, accessing the knowledge base, cross-referencing the waveform attributes with data in the knowledge base, cross-referencing the hemodynamic parameter input with data in the knowledge base, and outputting a suggested likelihood of a particular disease state based on the cross-referencing step. The method in accordance with the present invention optionally includes a display device for displaying the output. The knowledge base of the present invention can also include goal-directed therapies associated with particular disease states for providing suggested goal-directed therapies based on the cross-referencing of the waveform attributes and the hemodynamic parameters with the knowledge base.

The invention will be further described with reference to the following detailed description taken in conjunction with the drawings.

DETAILED DESCRIPTION

Figure 1:
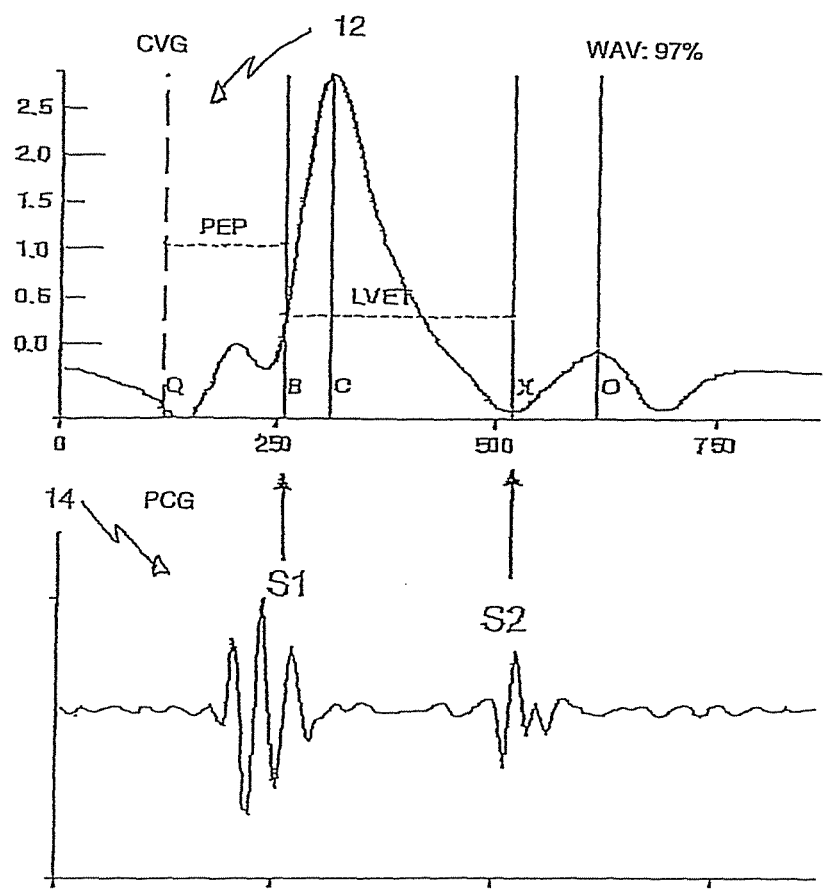
FIG. 1 represents CVG and PCG waveforms of a healthy patient.
Figure 2:
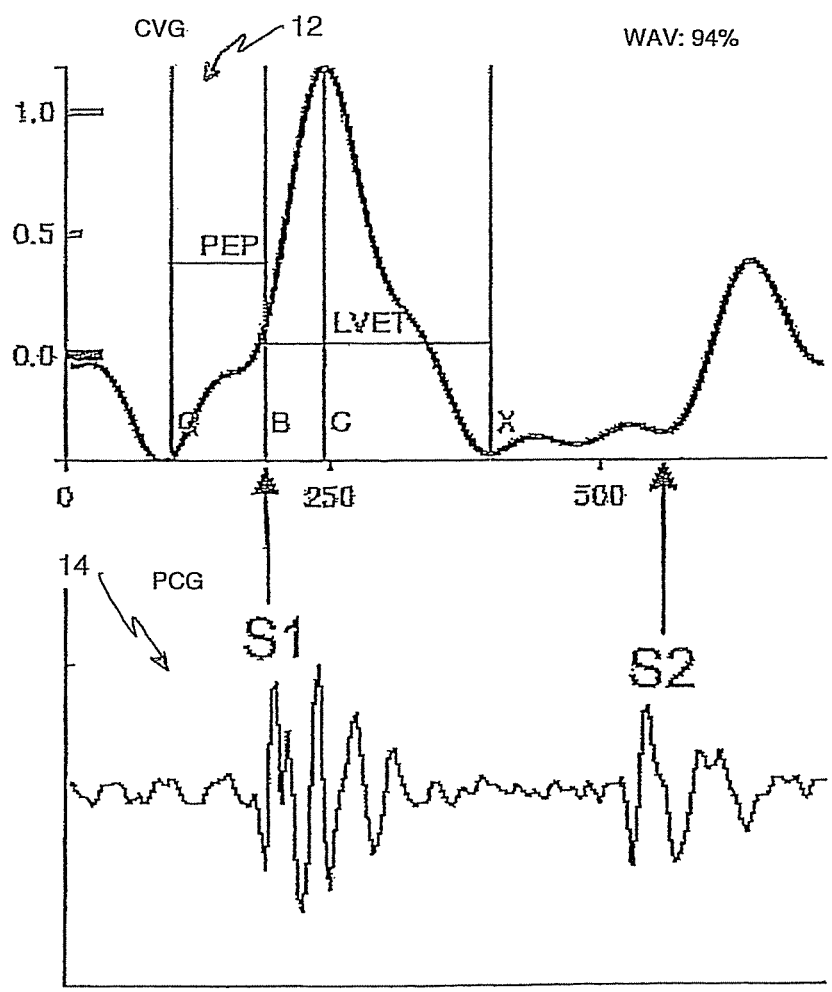
FIG. 2 represents CVG and PCG waveforms of an unhealthy patient.

Referring to FIGS. 1 and 2, there is shown a CVG waveform 12 and a PCG waveform 14 in accordance with the system and method of the present invention. Both figures depict heart valve activity in CVG waveform 12. The PEP is determined by identifying the time period between the starting point of the QRS complex based on an ECG signal, labeled as the Q point, and the starting point of the mechanical systole as marked by the initial deflection of the systolic waveform based on the ECG signal coincident with the opening of the aortic valve or the onset of left ventricular ejection into the aorta, labeled as the B point. The LVET is determined by identifying the time period between the end of the PEP and the closure of the aortic valve when ejection ends, labeled as the X point. Both figures also depict heart valve activity in PCG waveform 14, where known devices and methods are used to monitor and record sounds associated with the aortic valve opening, labeled as S1, and closing, labeled as S2. While FIGS. 1 and 2 depict PCG waveforms, those skilled in the art can appreciate that waveforms generated from any signals derived from heart valve activity can be depicted in relation to CVG waveforms.

Figure 3:
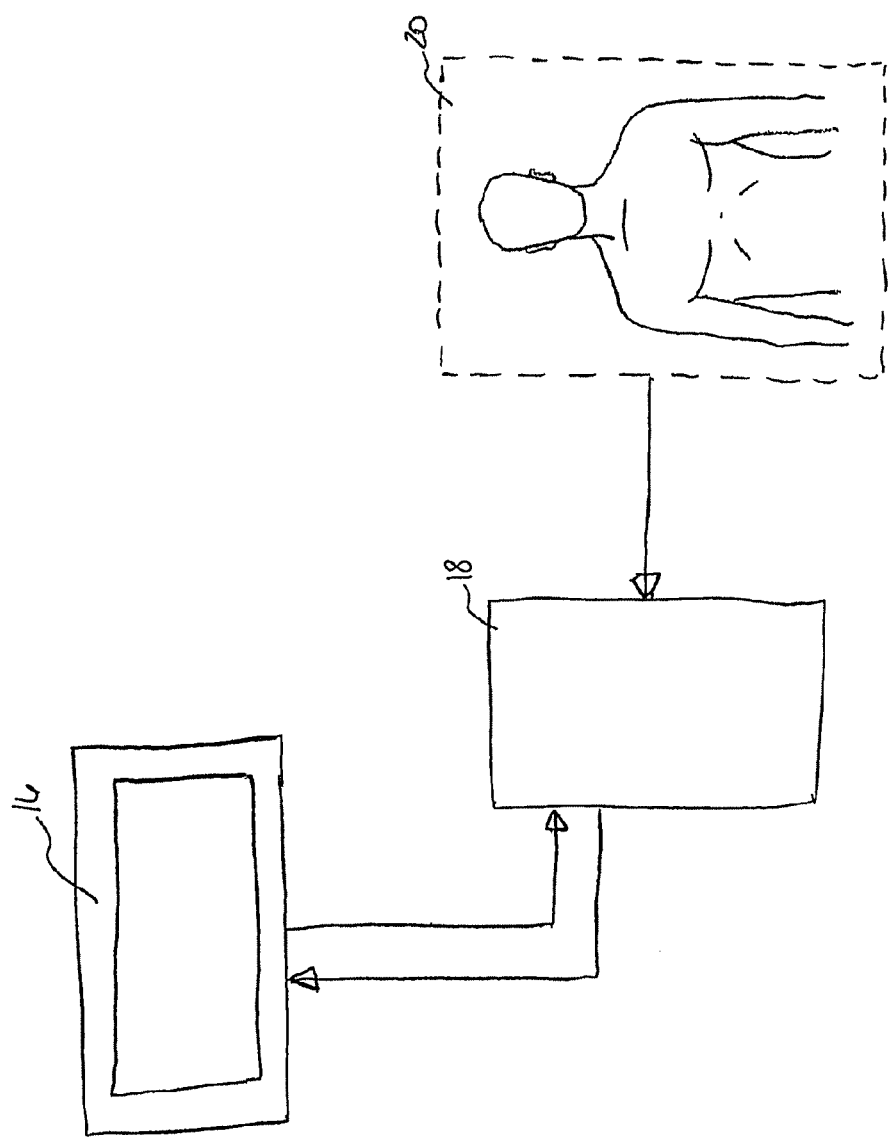
FIG. 3 is a schematic diagram of the system of the present invention illustrating the principal components thereof.

Referring to FIG. 3, one embodiment of the system in accordance with the present invention includes a display device 16 used to display cardiovasculograms and a processing device 18. Processing device is used to receive inputs from a sensor 20 hooked to a patient, generate cardiovasculograms and communicate with display device 16. Those skilled in the art can appreciate that display device 16 may include any type of device for presenting visual information such as, for example, a computer monitor or flat-screen display. Display device 16 may be equipped with user input devices, such as buttons for silencing audible alarms, erasing visual alarms or a combination thereof.

In one embodiment, sensor 20 includes electrodes for measuring ICG signals, PCG signals and ECG signals, microphones for measuring and recording heart sounds, blood pressure monitors, signals representing central venous pressure, finger plethysmographs and the like. While FIG. 3 depicts one sensor 20, in another embodiment more than one sensor 20 is used. Here, a first sensor is used to convert physiological data from a patient being monitored to a waveform having particular waveform attributes representing the physiological data. The first sensor can be an ICG system, an ECG system, a PCG system, or a combination thereof. An output generated from the first sensor can be a physical output, including but not limited to graphical display, printout, and the like. The output from the first sensor can alternately or simultaneously be an electrical output signal configured to be received by processing device 18. A second sensor is used to measure other hemodynamic parameters from the patient being monitored and convert them into a second output. These hemodynamic parameters include, but are not limited to thoracic fluid content (TFC), heart rate (HR), pre-ejection period (PEP), left ventricular ejection time (LVET), isovolumic relaxation time (IVRT), stroke volume (SV), cardiac output (CO), blood pressure, Heather Index (HI), and systemic vascular resistance (SVR). The second output generated from the second sensor can be a physical output, including but not limited to graphical display, printout, and the like. The second output from the second sensor can alternately or simultaneously be an electrical output signal configured to be received by processing device 18. Those skilled in the art can appreciate that the number and use of the sensors can vary. Those skilled in the art can appreciate that the system in accordance with the present invention may include stationary systems used in intensive care units or emergency rooms in hospitals, or may comprise portable units for use by emergency medical technicians in ambulances, at the scene of accidents, and when responding to other emergency situations.

Processing device 18 includes cardiovasculogram criteria for the diagnosis of heart failure based upon changes noted in the normal contours and dimensions of the typical cardiovasculogram waveform. While clinicians often use a subjective pattern recognition methodology for determination of aberrancy, the present invention includes objective criteria that can be utilized for a more exacting analysis. These objective criteria are useful in the development of a computerized algorithmic analysis of cardiovasculogram waveforms. Those skilled in the art can appreciate that the system may contain criteria for diagnoses of other disease states.

Figure 4:
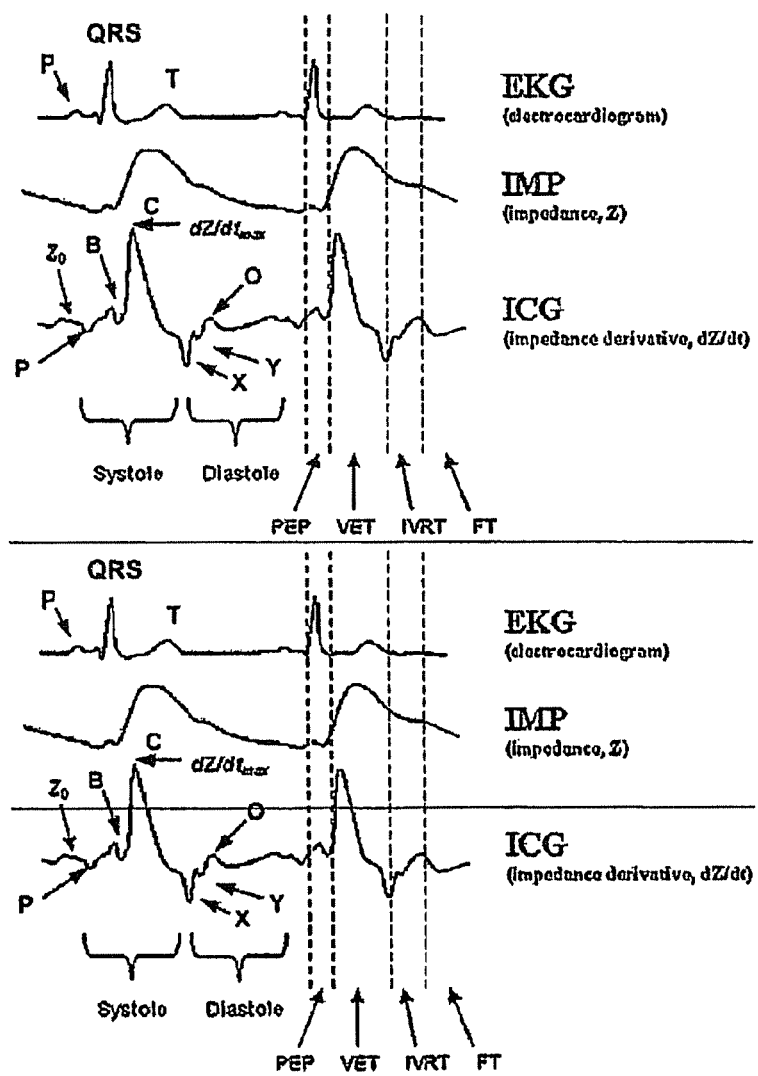
FIG. 4 represents common ECG and ICG signals.

Referring now to FIG. 4, there are shown waveform attributes, including baseline thoracic impedance ($Z_0$), atrial wave (A), aortic valve opening (B), maximum aortic flow (C) (also represented as $dZ/dt_{max}$), aortic valve closing (X); pulmonic valve closing (Y), mitral valve opening (O); pre-ejection period (PEP); ventricular ejection time (VET), isovolumic relaxation time (IVRT), and ventricular filling time (FT). These waveform attributes can be used to build the cardiovasculogram criterion for diagnosing heart failure based upon changes noted in the normal contours and dimensions of typical cardiovasculogram waveforms.

Still referring to FIG. 4, the C-wave is the major upward deflection in impedance seen during systolic phase of the cardiac cycle that peaks at the point of $dZ/dt_{max}$. It is seen as the first deflection from baseline thoracic impedance ($Z_0$) after the A-wave, beginning with the B point and ending with the X point. During systole, the form of the C-wave is based on the force of ventricular contraction and the resultant aortic pulse pressure wave generated when blood is transferred out of the ventricle and into the aorta. The $dZ/dt_{max}$ point of the C-wave is correlated with the peak aortic blood flow. Systolic function is generally defined by the shape, depth, and duration of the C-wave. Normal amplitudes for the C-wave will vary depending on the system used but may range from 1.05 to 2.70.

The O-wave is defined by the diastolic portion of the cardiac cycle and peaks at the point of mitral valve opening, shown as the 0 point on FIG. 4. The filling of the vena cava and pulmonary vein during the early phase of diastole results in the up-slope of the impedance signal. The ventricular filling phase begins when the tricuspid and mitral valves open. During the terminal portion of the O-wave, there is an increase in the impedance signal and a return to baseline thoracic impedance ($Z_0$) at the end of diastole as the venous system empties into the heart. Accordingly, this waveform reflects the events of diastole, including cardiac filling and venous return.

LVET begins at the end of the PEP when the aortic valve opens. The LVET ends at the closure of the aortic valve when ejection ends as determined by the dZ/dt waveform. A typical normal value for LVET is about 295±26 msec.

IVRT is a measure of diastolic function and active ventricular relaxation. IVRT is represented as the X to O period, which begins with the aortic valve closure and ends at the point of the maximum second deflection. A typical normal value for IVRT is less than 125 msec.

Figure 5:
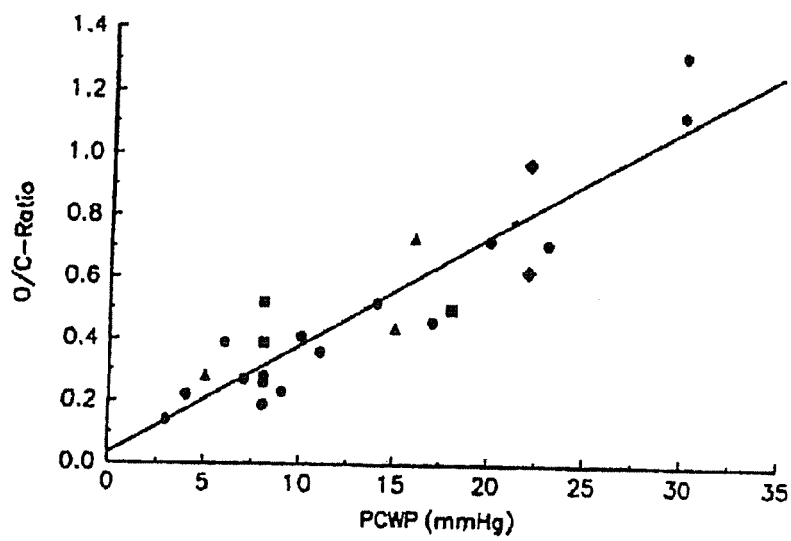
FIG. 5 represents a correlation between an O/C ratio, which is derived from an impedance cardiogram, and invasively measured pulmonary capillary wedge pressure (PCWP)

Referring now to FIG. 5, there is shown one embodiment for specific criteria used to interpret a heart failure waveform based on the foregoing attributes in accordance with the present invention. In one embodiment, specific criteria for determination of the proportional changes in the C-wave and O-wave in a patient with decompensated heart failure are based upon the correlation of the O/C ratio and the pulmonary capillary wedge pressure (PCWP). A typical normal range of the O/C ratio, i.e. 0.43±0.09, was correlated with a PCWP of about 10 to 12 mmHg, which is within typical normal PCWP range. Increases in the O/C ratio greater than 0.6±0.12 indicate pathologic congestion. This level of O/C ratio correlates with a PCWP of about 20 to 25 mmHg, which is considered the break point for the onset of pulmonary edema formation. Therefore, an O/C ratio of about greater than 0.6 can be used to indicate cardiopulmonary congestion as seen in acute decompensated heart failure.

Figure 6:
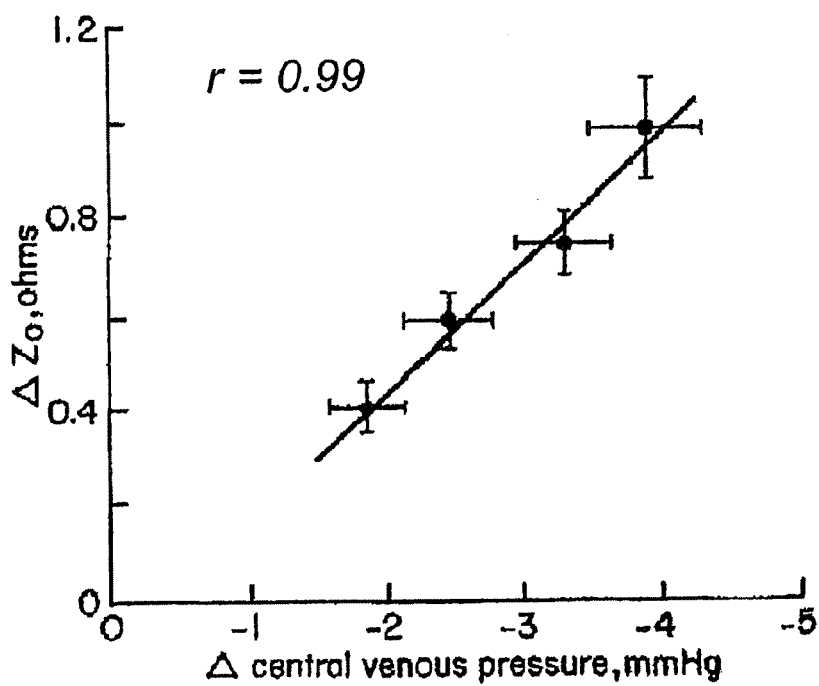
FIG. 6 represents a correlation between the change in baseline thoracic impedance $Z_0$ and the change in the central venous pressure.

Referring now to FIG. 6 there is shown another embodiment for specific criteria used to interpret a heart failure waveform in accordance with the present invention. Systolic heart failure is typically due to failure of in contraction strength of the myocardium during systole. Systolic contractile force can be viewed from a basic physical perspective, such as force=mass×acceleration, where systolic contractile force is defined as the amount of blood ejected, mass, times the velocity at which it is ejected, acceleration. In a normal CVG waveform, cardiac systole manifests as a sharp peaking C-wave (as shown in FIG. 4). The upslope of the C-wave and the length of the base of the LVET wave are both independently correlated with a general myocardial contractile state. A CVG waveform pattern with a broad blunted C-wave is characteristic of general heart failure in a patient and can be used to help differentiate that condition. The typically normal values for the C-wave and LVET as previously discussed herein are used in the determination of aberrancy. A decompensated systolic heart failure condition is expected to physiologically lead to congestion within the venous side of the circulatory system.

This congestion can be correlated with increasing thoracic fluid content and increasing baseline thoracic impedance ($Z_O$) in the CVG waveform as depicted in FIG. 6. Large O-waves with elevated peaks are common in CVG waveforms depicting decompensated heart failure.

Figure 7:
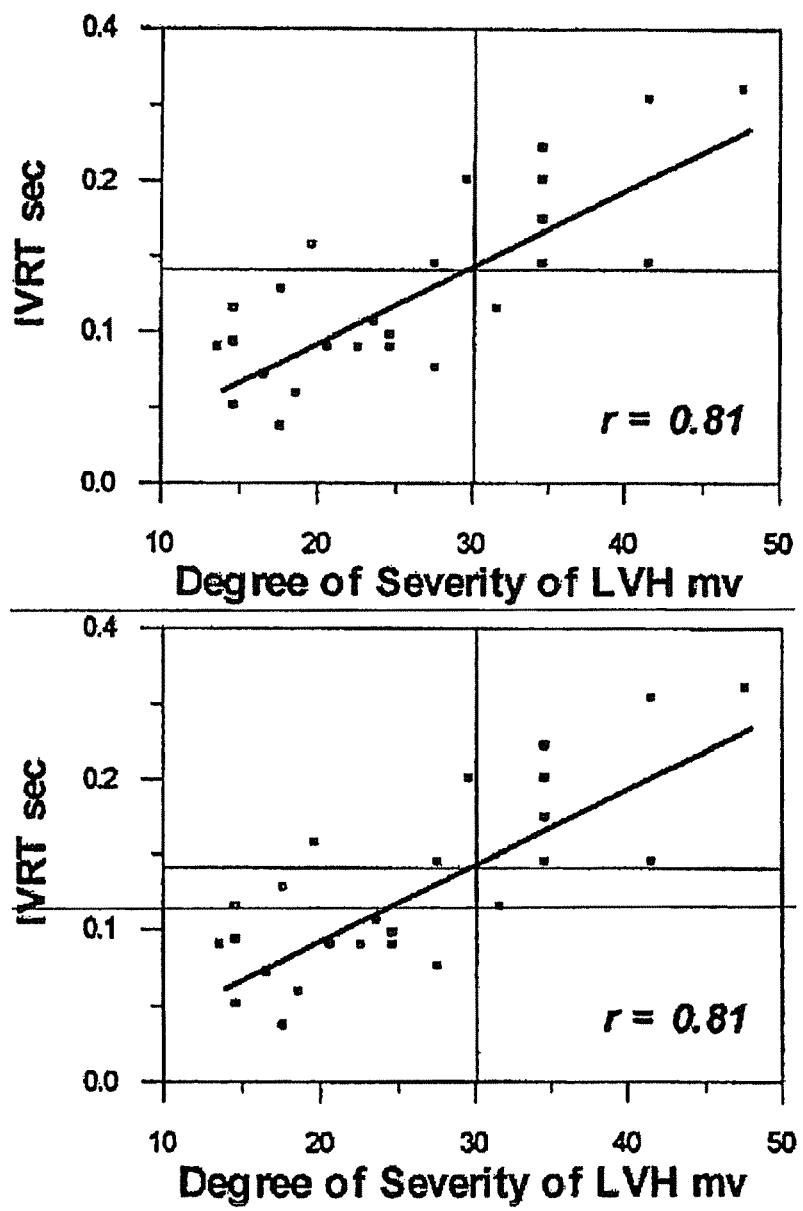
FIG. 7 represents a correlation between degree of severity of left ventricular hypertrophy (LVH) and isovolumic relaxation time (IVRT)

Referring now to FIG. 7, there is depicted another embodiment for specific criteria used to interpret a heart failure waveform in accordance with the present invention. A correlation between left ventricular hypertrophy measured in mV and active ventricular relaxation time measured in seconds can be used when assessing diastolic heart failure. Diastolic heart failure is caused by a limitation in ventricular compliance and relaxation, resulting in a limitation in cardiac filling during diastole. The diastolic IVRT can be measured from the O-wave of the CVG. Prolongation in the IVRT is indicated by a general pattern of a widening of the base of the O-wave, which suggests a diagnosis of diastolic heart failure. As shown in FIG. 7, IVRT by CVG waveform analysis can be correlated with the degree of left ventricular hypertrophy, a major determinant of diastolic dysfunction. When there is concurrent venous congestion due to the delay in cardiac filling during diastole combined with the occurrence of decompensation, the O-wave pattern may also have an elevated peak. This combination of factors provides a general CVG waveform pattern characterized by an overall substantial and prolonged O-wave with a large area under the curve. This type of O-wave may be indicative of decompensated diastolic heart failure. Normal values for the O-wave and IVRT, as previously discussed, can be used for determination of aberrancy.

Figure 8:
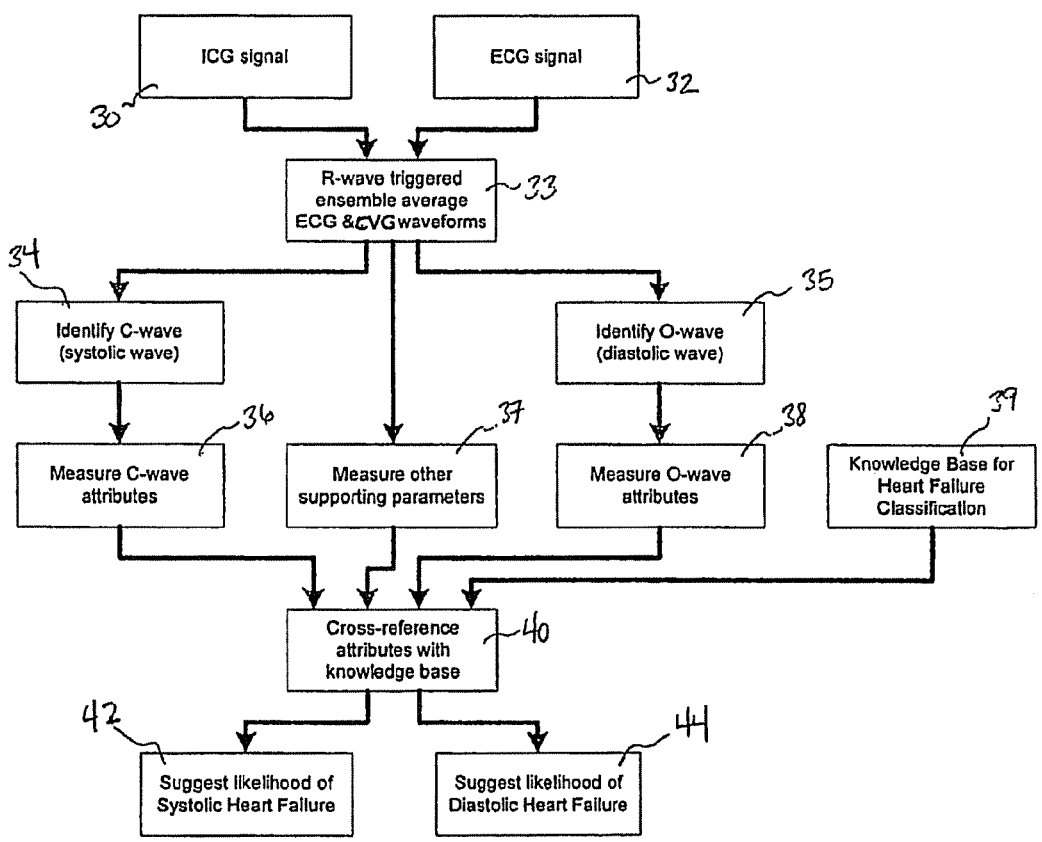
FIG. 8 is a flowchart illustrating one method for using cardiovasculogram (CVG) criteria for the diagnosis of heart failure.

As illustrated in the flowchart depicted in FIG. 8, one method for using CVG criterion for the diagnosis of heart failure in accordance with the present invention includes: inputting an ICG signal 30; inputting an ECG signal 32; compiling an R-wave triggered ensemble average based on ECG and ICG signals 33; producing a CVG waveform; identifying the C, or systolic, wave 34; identifying the O, or diastolic, wave 35; measuring C-wave attributes 36; measuring other supporting parameters 37; measuring O-wave attributes 38; inputting knowledge base for heart failure classification 39; cross-referencing C-wave and O-wave attributes and other supporting parameters with knowledge base 40; suggesting the likelihood of systolic heart failure 42; and suggesting the likelihood of diastolic heart failure 44. Those skilled in the art can appreciate that cross-referencing of the measured attributes with the knowledge base can be accomplished by Bayesian probability statistics, fuzzy logic, or other advanced mathematical techniques. While FIG. 8 shows the use of an R-wave triggered ensemble average, those skilled in the art can appreciate that other waveform averaging techniques, non-averaged waveforms and/or various compilations of waveforms and/or multi-beat sequences of waveforms can be used in accordance with the present invention. The term knowledge base as used herein is defined as a database, a computer program, any type of data readable by an electronic medium, any data (whether or not alphanumeric) that can be indexed and stored in an electronic medium, data stored in hard copy that can be accessed by or entered into the system of the present invention by users, and the like.

In the flowchart depicted in FIG. 8, the C-wave attributes and O-wave attributes that could be measured in steps 36 and 38 include, but are not limited to, amplitude, duration, upward slope, downward slope, shape, depth, area, tone and presence of additional peaks. Other supporting parameters that could be measured in step 37 include, but are not limited to, thoracic fluid content (TFC), heart rate (HR), pre-ejection period (PEP), left ventricular ejection time (LVET), systolic time ratio, isovolumic relaxation time (IVRT), stroke volume (SV), stroke volume index, cardiac output (CO), cardiac index, blood pressure, Heather Index (HI), rate pressure product, ejection fraction, end diastolic volume, pulmonary artery occlusion pressure, central venous pressure and systemic vascular resistance (SVR). FIG. 8 depicts the use of PCG signals and other supporting parameters to confirm heart valve activity in the CVG waveform for illustrative purposes only. Those skilled in the art can appreciate that PCG signals and/or other supporting parameters could be used alone or in combination to confirm heart valve activity in CVG waveforms.

In step 40, waveform attributes and other supporting parameters are cross-referenced against a knowledge base containing known attributes of heart failure classifications. Cross-reference logic for identifying likelihood of systolic heart failure and diastolic heart failure, including assessing C-wave parameters, O-wave parameters, and supporting parameters, is included in processing device 18. In one embodiment, the logic could also be used to assess cross-factors. One exemplary cross-factor is the ratio of the O-wave height to C-wave height. Those skilled in the art can appreciate that cross-referencing of the measured attributes with the knowledge base can be accomplished by Bayesian probability statistics, fuzzy logic, or other advanced mathematical techniques.

In one embodiment, the suggestion of the likelihood of systolic heart failure in step 42 or diastolic heart failure in step 44 could be presented with confidence information in a numeric, graphical, bar presentation, or other format. In another embodiment, the suggestion of the likelihood of systolic heart failure in step 42 or diastolic heart failure in step 44 could be associated with the likelihood or coincidence of waveform attributes being associated with a standardized heart failure classification system such as the New York Heart Association (NYHA) classification system.

Figure 9:
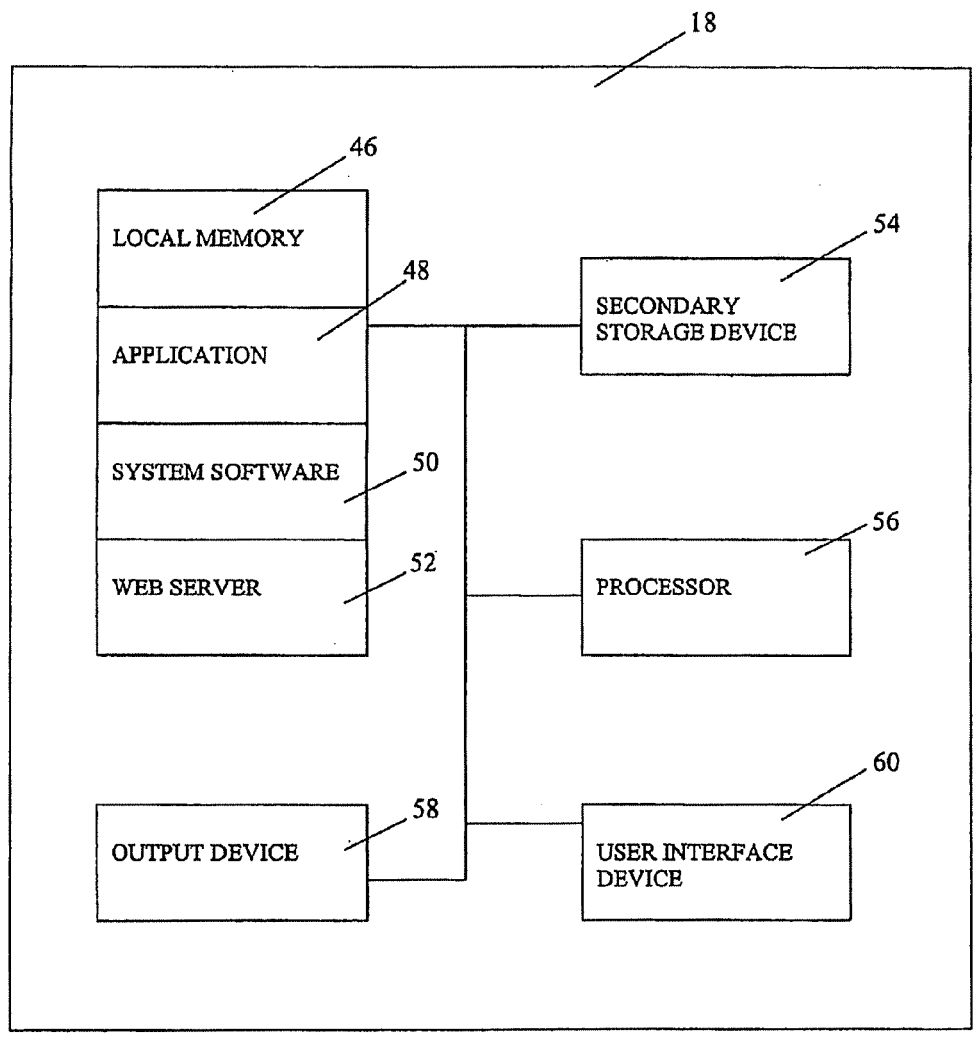
FIG. 9 is a block diagram of the exemplary components of an electronic processing device used in accordance with the system of the present invention.

Referring now to FIG. 9, processing device 18 illustrates typical components of a processing device. Processing device 18 includes a local memory 46, a secondary storage device 54, a processor 56, a user interface device 60 and an output device 58. Local memory 46 may include random access memory (RAM) or similar types of memory, and it may store one or more applications 48, including system software 50, and a web server 52, for execution by processor 56. Local memory 46 is generally located in individual pieces of equipment used to monitor cardiac performance of patients. Secondary storage device 54 may include a hard disk drive, floppy disk drive, CD-ROM drive, or other types of non-volatile data storage. The local cache that includes a patient's CVG data may be stored on secondary storage device 54. Processor 56 may execute system software 50 and other applications 48 stored in local memory 46 or secondary storage 54. Processor 56 may execute system software 50 in order to provide the functions described in this specification including, but not limited to, measuring, reporting, displaying and comparing cardiovasculograms. User interface device 60 may include any device for entering information into processing device 18, such as a keyboard, mouse, cursor-control device, touch-screen, infrared, microphone, digital camera, video recorder, or any other instrument or device necessary to measure, report, display and compare cardiovasculograms. Output device 58 may include any type of device for presenting a hard copy of information, such as a printer, and other types of output devices including speakers or any device for providing information in audio form.

Web server 52 is used to provide access to patient data stored in memory 46 and on secondary storage devices 54 and display the data. Web server 52 allows users secure remote access to the system through which they can monitor the status of a patient's CVG data and access patient data. Web server 52 can allow access to a user running a web browser. Any web browser, co-browser, or other application capable of retrieving content from a network and displaying pages or screens may be used.

Examples of processing devices 18 for interacting within the impedance cardiography system include embedded microprocessors, digital signal processors, personal computers, laptop computers, notebook computers, palm top computers, network computers, Internet appliances, or any processor-controlled device capable of storing data, system software 50 and any other type of application 48 stored in local memory 46 or accessible via secondary storage device 54.

Figure 10:
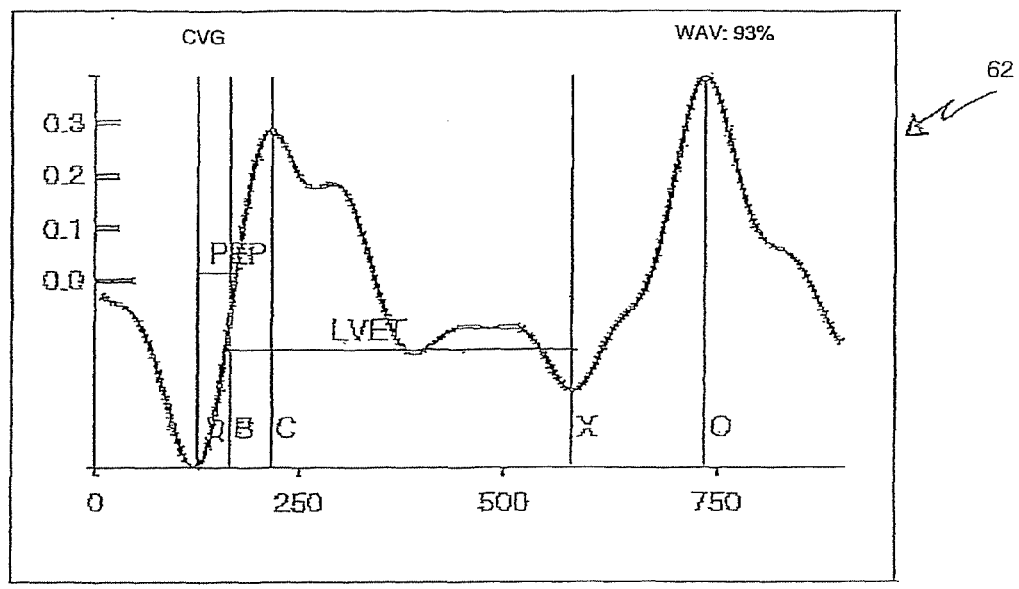
FIG. 10 represents an CVG waveform of a patient with systolic heart failure.
Figure 11:
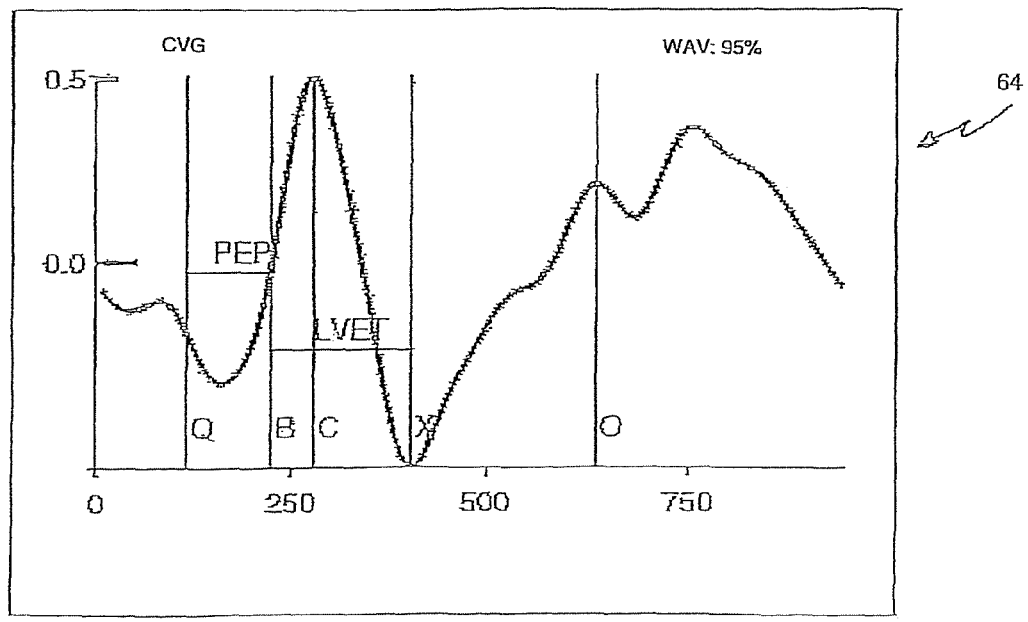
FIG. 11 represents an CVG waveform of a patient with diastolic heart failure.
Figure 12:
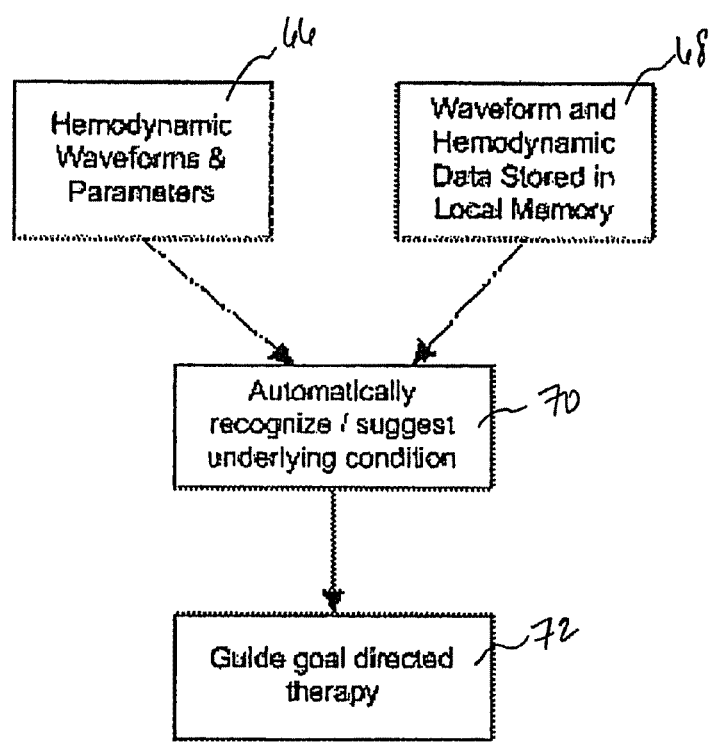
FIG. 12 is a flowchart illustrating one method of correlating measured cardiovasculograms with known cardiovasculograms in accordance with the present invention.

Local memory 46 can further include an application for using the knowledge base for heart failure classification in step 39 of FIG. 8. This application is used to provide automated recognition of hemodynamic parameters and waveform attributes. One method includes saving waveforms and hemodynamic parameters in local memory 46 to be used in the aforementioned methods as depicted in FIGS. 5-7 and as templates for future comparison and identification of associated disease states. For example, a patient having CVG waveform 62 as depicted in FIG. 6 was diagnosed by an experienced healthcare professional as having systolic heart failure. A patient having CVG waveform 64 as depicted in FIG. 11 was diagnosed by an experienced healthcare professional as having diastolic heart failure. These waveforms 62 and 64 are stored as waveform and hemodynamic data in local memory 46. The method illustrated in FIG. 12 can incorporate the stored waveforms and hemodynamic data depicted in FIGS. 10 and 11 and includes: measuring CVG waveform and hemodynamic parameters of a new patient 66; providing access to a knowledge base of waveform attributes and hemodynamic parameter data stored in local memory 68; automatically correlating the new patient CVG waveform attributes and hemodynamic parameters to at least one record stored in local memory 70; and guiding a goal directed therapy for a possible disease based on this correlation 72.

While FIG. 8 depicts the application for using the knowledge base for heart failure classification included in processing device 18, those skilled in the art can appreciate that processing device 18 and knowledge base can be two or more separate systems that communicate with one another via known communication techniques, including but not limited to modem connections, wireless connections, optical connections and the like.

Figure 13:
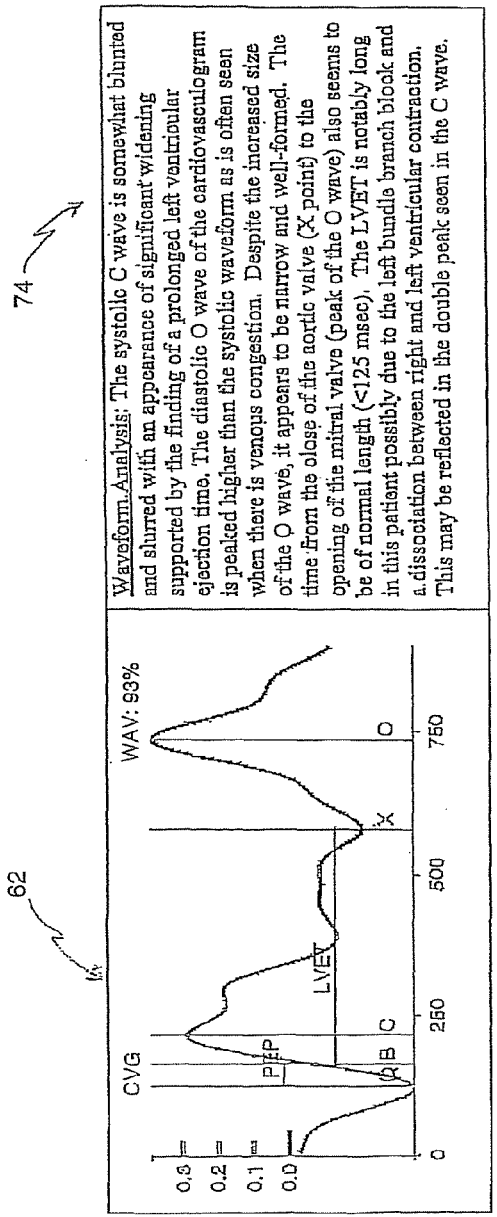
FIG. 13 represents the CVG waveform shown in FIG. 10 with additional information from an experienced healthcare professional.
Figure 14:
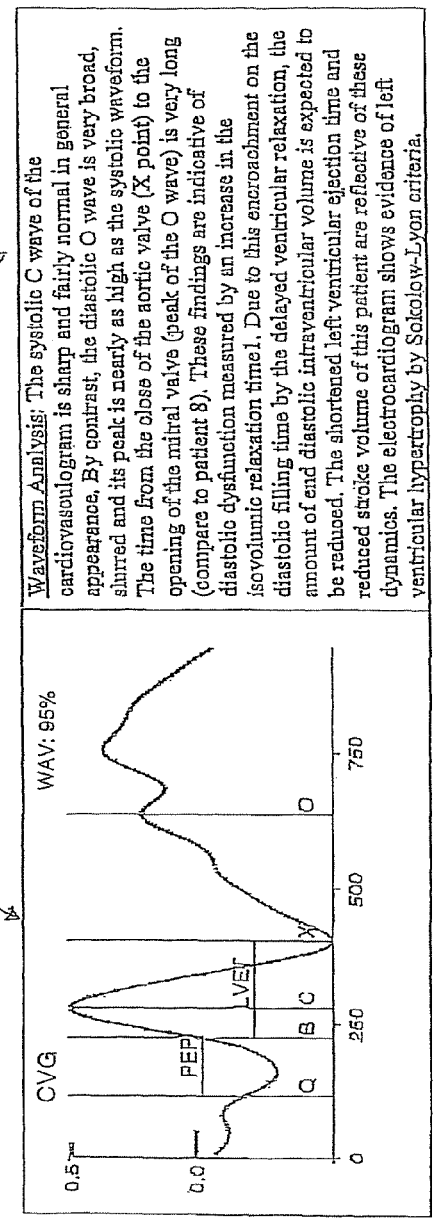
FIG. 14 represents the CVG waveform shown in FIG. 11 with additional information from an experienced healthcare professional.

In another embodiment, certain waveform attributes may be learned from waveforms associated with disease states, where combinations of these attributes are used to form a template for that disease state. In yet another embodiment, analysis and diagnoses for various disease states as determined by experienced healthcare professionals can be correlated with saved waveforms attributes and hemodynamic parameters. For example, as shown in FIG. 13, an experienced healthcare professional can input specific information 74 about waveform 62 (also shown without information in FIG. 10) correlated with systolic heart failure. In addition, as shown in FIG. 14, an experienced healthcare professional can input specific information 76 about waveform 64 (also shown without information in FIG. 11) correlated with diastolic heart failure. These waveforms and hemodynamic data along with additional information can be stored in local memory 46. When a new waveform is generated, it can be compared to the information stored in local memory 46 and healthcare professionals can utilize all of the information, as well as the waveforms and hemodynamic data, to diagnose a possible disease. In this manner, less experienced healthcare professionals get the benefit of experienced healthcare professionals in recognizing and diagnosing a possible disease based on waveform attributes, hemodynamic parameters and/or other information. In addition, recognition and diagnosis of a possible disease can occur quicker based on past diagnoses. The method can optionally further provide healthcare professionals with assistance in achieving a goal directed therapy.

While the waveforms depicted in FIGS. 10, 11, 13 and 14 are CVG waveforms, those skilled in the art can recognize that this method may be used on any type of waveform. Those skilled in the art can also recognize that this method may be used with CVGs that correlate ICG signals with any signals derived from heart valve activity, hemodynamic events and any other combination thereof.

While the invention has been described with reference to the specific embodiments thereof, those skilled in the art will be able to make various modifications to the described embodiments of the invention without departing from the true spirit and scope of the invention. The terms and descriptions used herein are set forth by way of illustration only and are not meant as limitations. Those skilled in the art will recognize that these and other variations are possible within the spirit and scope of the invention as defined in the following claims and their equivalents.

What is claimed is:

1. A system for automated recognition of hemodynamic parameters and waveform attributes comprising:
   an impedance cardiography device including at least one sensor configured to be externally placed on a patient and adapted to noninvasively provide at least one impedance waveform signal;
   a knowledge base including known data corresponding to various disease states;
   a processing device in operable communication with said at least one sensor and said knowledge base, said processing device configured to receive said at least one impedance waveform signal and calculate a hemodynamic parameter of the patient therefrom, identify waveform attributes on said waveform signal, measure said waveform attributes, measure said hemodynamic parameter, and cross-reference said waveform attributes and said hemodynamic parameter with said knowledge base data, and output a suggested likelihood of a particular disease state based on said cross-reference.

2. The cardiography system of claim 1 further comprising a display device configured to display at least said output.

3. The cardiography system of claim 2 wherein said display device is selected from the group consisting of computer monitor, flat-screen display, projector, printing device, and audible device.

4. The cardiography system of claim 2 wherein said display device further comprises user input devices configured to communicate with said display device and said processing device.

5. The cardiography system of claim 1 wherein said knowledge base known data further comprises goal directed therapies correlated with particular disease states.

6. The cardiography system of claim 5 wherein said processing device is configured to output at least one suggested goal directed therapy based on the suggested likelihood of a particular disease state.

7. The cardiography system of claim 1 wherein said impedance waveform signal is selected from the group consisting of an ICG signal, an ECG signal and a PCG signal.

8. The cardiography system of claim 1 wherein said hemodynamic parameter is selected from the group consisting of thoracic fluid content, heart rate, pre-ejection period, left ventricular ejection time, systolic time ratio, isovolumic relaxation time, stroke volume, stroke volume index, cardiac output, cardiac index, blood pressure, Heather Index, rate pressure product, ejection fraction, end diastolic volume, pulmonary artery occlusion pressure, central venous pressure and systemic vascular resistance.

9. The cardiography system of claim 1 wherein said knowledge base known data comprises a plurality of waveforms, waveform attributes and hemodynamic parameters.

10. The cardiography system of claim 9 wherein said plurality of waveforms, waveform attributes and hemodynamic parameters are associated with systolic heart failure.

11. The cardiography system of claim 9 wherein said plurality of waveforms, waveform attributes and hemodynamic parameters are associated with diastolic heart failure.

12. The cardiography system of claim 1 wherein said processing device is selected from the group consisting of embedded microprocessors, digital signal processors, personal computers, laptop computers, notebook computers, palm top computers, network computers, Internet appliances, and processor-controlled devices configured to store data and software.

13. The cardiography system of claim 1 said processing device being configured to create an ensemble average waveform based on said waveform signal.

14. The cardiography system of claim 13 said processing device being configured to identify and measure waveform attributes on said ensemble average waveform.

15. The cardiography system of claim 14 said processing device further configured to cross-reference said waveform attributes from said ensemble average waveform with said knowledge base known data.

16. The cardiography system of claim 15 said processing device being configured to output a suggested likelihood of a particular disease state.

17. A method for automated recognition of hemodynamic parameters and waveform attributes to assess disease states comprising:
providing an impedance cardiography system for the automated recognition of hemodynamic parameters and waveform attributes to assess disease states;
externally placing a sensor on a patient, said sensor for non-invasively generating an impedance waveform signal;
providing a knowledge base including known data corresponding to various disease states;
providing a processing device operably communicating with said at least one sensor and said knowledge base, said processing device for receiving said impedance waveform signal and calculating a hemodynamic parameter of the patient therefrom, identifying waveform attributes on said waveform signal, measuring said waveform attributes, measuring said hemodynamic parameter, accessing said knowledge base, cross-referencing said waveform attributes with data in said knowledge base, cross-referencing said hemodynamic parameter with data in said knowledge base, and outputting a suggested likelihood of a particular disease state based on said cross-referencing.

18. The method of claim 17 further comprising providing a display device for displaying said outputting.

19. The method of claim 18 further comprising said knowledge base further providing goal directed therapies correlated with particular disease states.

20. The method of claim 19 further comprising said processing device outputting at least one suggested goal directed therapy based on the suggested likelihood of a particular disease state.

21. The method of claim 18 wherein said display device is selected from the group consisting of computer monitor, flat-screen display, projector, printing device, and audible device.

22. The method of claim 18 wherein said display device further comprises user input devices configured to communicate with said display device and said processing device.

23. The method of claim 17 wherein said impedance waveform signal is selected from the group consisting of an ICG signal, an ECG signal and a PCG signal.

24. The method of claim 17 wherein said hemodynamic parameter is selected from the group consisting of thoracic fluid content, heart rate, pre-ejection period, left ventricular ejection time, systolic time ratio, isovolumic relaxation time, stroke volume, stroke volume index, cardiac output, cardiac index, blood pressure, Heather Index, rate pressure product, ejection fraction, end diastolic volume, pulmonary artery occlusion pressure, central venous pressure and systemic vascular resistance.

25. The method of claim 17 wherein said knowledge base known data comprises waveforms, waveform attributes and hemodynamic parameters.

26. The method of claim 25 wherein said waveforms, waveform attributes and hemodynamic parameters are associated with systolic heart failure.

27. The method of claim 25 wherein said waveforms, waveform attributes and hemodynamic parameters are associated with diastolic heart failure.

28. The method of claim 17 wherein said processing device is selected from the group consisting of embedded microprocessors, digital signal processors, personal computers, laptop computers, notebook computers, palm top computers, network computers, Internet appliances, and processor-controlled devices configured to store data and software.

29. The method of claim 17 further comprising said processing device creating an ensemble average waveform based on said waveform signal.

30. The method of claim 29 further comprising said processing device identifying and measuring waveform attributes on said ensemble average waveform.

31. The method of claim 30 further comprising said processing device cross-referencing said waveform attributes from said ensemble average waveform with data in said knowledge base.

32. The method of claim 31 further comprising said processing device outputting a suggested likelihood of a particular disease state.

* * * * *